US00PP13688P29

(12) United States Plant Patent
Heims

(10) Patent No.: US PP13,688 P2
(45) Date of Patent: Apr. 1, 2003

(54) TRICYRTIS PLANT NAMED 'GILTY PLEASURE'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 09/967,088

(22) Filed: Sep. 27, 2001

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—Annette H. Para
(74) *Attorney, Agent, or Firm*—Klarquist Sparkman, LLP

(57) ABSTRACT

A new and distinct hybrid of *Tricyrtis formosana* plant characterized by a vigorous habit, gold colored leaves and purple spotted flowers.

2 Drawing Sheets

BOTANICAL CLASSIFICATION

*Tricyrtis formosana.*

VARIETY DENOMINATON

'Gilty Pleasure'.

The present invention relates to a new and distinct hybrid of *Tricyrtis formosana*, of the family Liliaceae, which originated as a chimeral separation in tissue culture from *Tricyrtis formosana* 'Gilt Edge' (an unpatented plant).

The new variety has been reproduced only by asexual propagation (division and tissue culture). Each of the progeny exhibits identical characteristics to the original plant.

This plant is characterized by the following:

1. Gold colored leaves.
2. Vigor and clean appearance.
3. Attractive purple spotted flowers with a yellow throat.

Asexual propagation by division and tissue culture as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

Sheet 1 shows Tricyrtis 'Gilty Pleasure' growing in a pot in a cool greenhouse in Canby, Oreg.

Sheet 2 shows a one-year old Tricyrtis 'Gilty Pleasure' in the garden in September.

DETAILED PLANT DESCRIPTION

Figure 1:
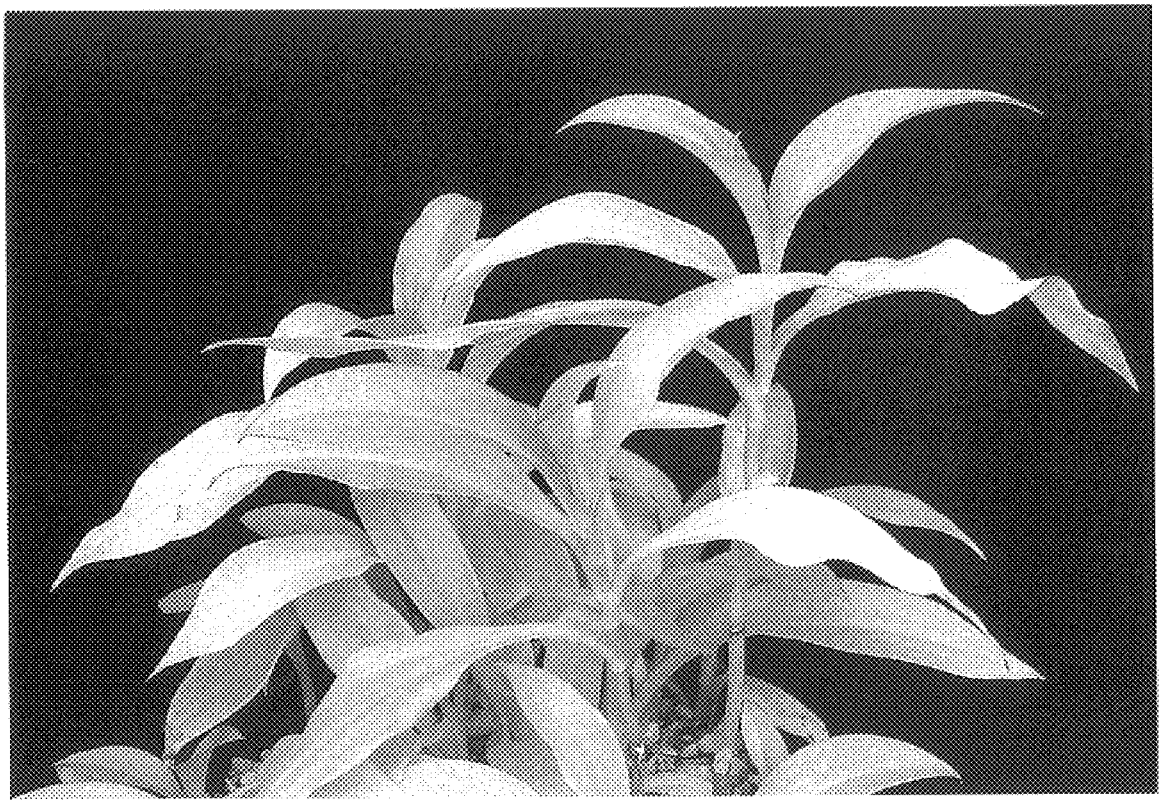
Figure 2:
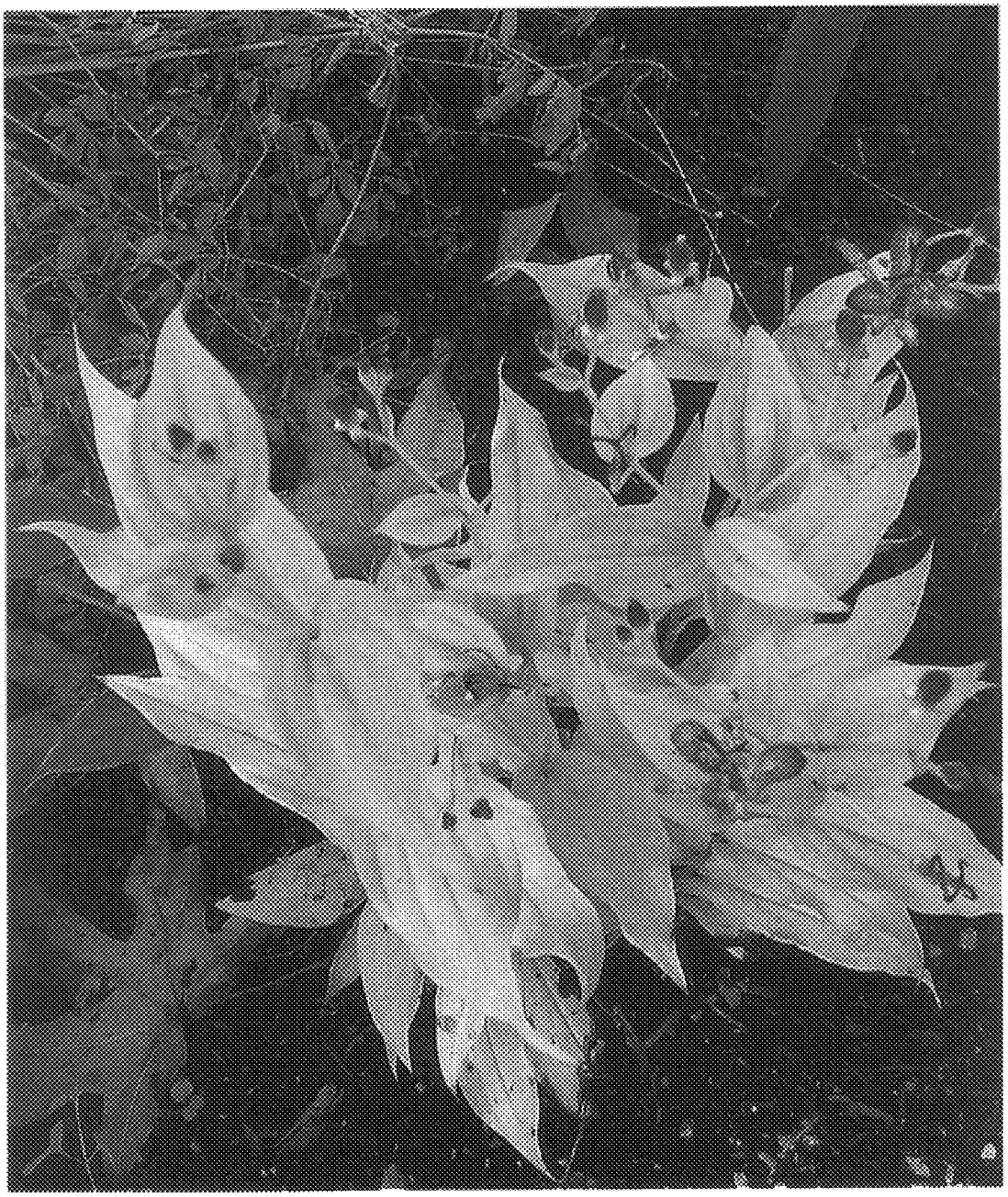

The following is a detailed description of the new *Tricyrtis formosana* cultivar based on observations of a three year old specimen grown in a two gallon pot in the greenhouse in Canby, Oreg. The color descriptions are all based on *The Royal Horticultural Society Colour Chart*.

Plant:
- *Type.*—Herbacous perennial.
- *Hardiness.*—USDA Zones 6 to 9.
- *Size.*—30 cm. wide and 15 cm. tall.
- *Form.*—With short rhizomes forming a compact clump.

Stem:
- *Type.*—Non branching, caulescent. Mostly erect and sometimes arching.
- *Size.*—To 40 cm long and 4 cm wide with swollen nodes.
- *Surface.*—Pubescent on young growth.
- *Stem number.*—36.
- *Color.*—Yellow Green 145A.

Leaf:
- *Type.*—Simple.
- *Shape.*—Variable. Oblanceolate at base of stem to elliptic to ovate at the top.
- *Arrangement.*—Alternate.
- *Blade length.*—Grows to 11.5 cm.
- *Blade width.*—4.3 cm. at the widest part.
- *Margins.*—Entire.
- *Apex.*—Acuminate.
- *Base.*—Clasping.
- *Texture.*—Pubescent.
- *Venation.*—Parallel.
- *Color.*—Young leaves: Yellow Green 145A top and bottom. Mature leaves: Yellow Green 151A with the veins Yellow Green 144A and the bottom sides between Yellow Green 144A and 146A.

Inflorescence:
- *Type.*—Terminal cymes.
- *Pedicel.*—Length: Grows from 1 to 3 cm. long. Texture: Pubescent.
- *Bloom time.*—July to October.

Flower bud:
- *Size.*—2.2 cm. deep and 0.7 cm. wide.
- *Shape.*—Oblong, wider near the top with two lobed, saccate spurs at the base.
- *Color.*—Purple, Red Purple 71A on top half and Yellow 4C to spurs. Spurs are Greyed Purple 184C with tips Yellow Green 153A.

Flower:
- *Type.*—Actinomorphic, upfacing, with segments free.
- *Shape.*—Funnelform.
- *Size.*—Grows to 2.4 cm. deep and 2 cm. wide.
- *Texture.*—Glabrous.
- *Color.*—White 155A heavily spotted Red Purple 71A with a Yellow 4C eye. Spurs are as above.
- *Petal.*—Number — 3. Shape — Flat, strap shaped. Size — 2.4 cm long and 0.3 cm wide. Color — Inside: Red Purple 70A at tips to White 155A heavily spotted with Red Purple 70A with the spots showing through to outside. Base is Yellow 4C. Outside: Red Purple 70A to 155A with Red Purple 70A spots.

*Calyx.*—Petaloid, recurves slightly.

*Sepal.*—Number — 3. Shape — Oblanceolate, basally saccate with a mucronate tip. Size — 2.5 cm long and 0.7 cm wide. Color — Inside: Greyed Purple 187A on tip edge to Red Purple 70D with Red Purple 70A spots to Yellow 11A to D with some spots to Yellow Green 153A on spurs. Outside: Greyed Purple 187A to Red Purple 70A to White 155A with spots 70A showing through to Yellow White 158B.

*Pistil.*—2.1 cm. long.

*Stigma.*—3 parted, two branched, Red Purple 59A.

*Style.*—Heavily spotted Red Purple 59A.

*Filaments.*—1.7 cm long, purple spotted.

*Pollen color.*—Greyed Yellow 162A.

*Fragrance.*—None.

Fruit: None produced to date.

Seed: None produced to date.

Disease: None observed on plant grown under commercial conditions in Canby, Oreg.

COMPARISONS TO SIMILAR TRICYRTIS

Compared to *Tricyrtis formosana* 'Gates of Heaven', an unpatented plant, our new cultivar is more vigorous and does not die back or burn at the edges.

I claim:

1. A new and distinct hybrid of *Tricyrtis formosana* plant substantially as shown and described, characterized by gold colored leaves, vigor and purple spotted flowers.

* * * * *